United States Patent [19]

Dodd

[11] 4,187,255

[45] Feb. 5, 1980

[54] PROCESS FOR METHYLATING NAPHTHALENE

[75] Inventor: John R. Dodd, Ponca City, Okla.

[73] Assignee: Conoco, Inc., Ponca City, Okla.

[21] Appl. No.: 935,285

[22] Filed: Aug. 21, 1978

[51] Int. Cl.$^2$ .......................................... C07C 15/24
[52] U.S. Cl. .................................................. 585/467
[58] Field of Search .................................... 260/668 A

[56] References Cited

U.S. PATENT DOCUMENTS 3,993,701   11/1976   Leach et al. ...................... 260/621 R

OTHER PUBLICATIONS

Walter M. Kutz et al, J. Amer. Chem. Soc. 67, pp. 1312–1315, 1945.

Primary Examiner—Veronica O'Keffe
Attorney, Agent, or Firm—Bayless E. Rutherford, Jr.

[57] ABSTRACT

Broadly, the present invention is directed to a process for preparing 1-methylnaphthalene and 2-methylnaphthalene wherein the process comprises reacting naphthalene and methanol in the vapor phase at elevated temperatures and optionally under pressure in the presence of an effective amount of activated alumina catalyst. In a preferred embodiment the invention is directed to a process for preparing 2-methylnaphthalene in high selectivity by reacting naphthalene and methanol in the vapor phase at elevated temperatures in the range of about 500° to about 650° C. in the presence of an effective amount of activated alumina catalyst.

11 Claims, No Drawings

PROCESS FOR METHYLATING NAPHTHALENE

FIELD OF THE INVENTION

The invention is in the general field of methylating naphthalene. More specifically, the invention is in the field of preparing 2-methylnaphthalene in high selectivity using methanol as the alkylating agent and conducting the process at an optimum elevated temperature.

GENERAL BACKGROUND

Both 1-methylnaphthalene and 2-methylnaphthalene are useful materials of commerce. 2-methylnaphthalene can be oxidized to vitamin $K_3$ (menadione). 1-methylnaphthalene is useful as a fuel additive, as a plasticizer in polyvinyl chloride, as an intermediate for preparing rubber additives and as an intermediate for preparing fungicides.

The preparation of 1-methylnaphthalene and 2-methylnaphthalene by reacting methyl chloride with naphthalene using alumina catalyst is known [J. Am. Chem. Soc. 67, 1312-15 (1945)]. This article states that the optimum temperature was 400° C.

The use of methanol, instead of methyl chloride, as an alkylating agent provides several advantages. Usually, it does not produce a product with as much polyalkylate as alkylation with methyl chloride does. Use of methyl chloride results in hydrogen chloride (HCl) as a coproduct. HCl is known to be corrosive and toxic. On the other hand, the only coproduct with the use of methanol as the alkylating agent is water, which is innocuous. Methanol is less toxic than methyl chloride, particularly as an atmospheric contaminant. Since methanol is a liquid, it is easier to handle and to contain than methyl chloride, which is a gas under normal conditions. Moreover, methanol is less expensive than methyl chloride on a mole basis.

I have discovered a process for making 1-methylnaphthalene and 2-methylnaphthalene which used methanol.

Furthermore, surprisingly I have found a process for preparing 2-methylnaphthalene in high selectivity which uses methanol. The temperature of this process is considerably higher than that taught by the prior art using methyl chloride.

BRIEF SUMMARY OF THE INVENTION

Broadly stated, the present invention is directed to a process for preparing 1-methylnaphthalene and 2-methylnaphthalene wherein the process comprises reacting methanol and naphthalene in the vapor phase at a temperature in the range of about 425° to about 700° C. in the presence of an effective amount of activated alumina catalyst.

In a preferred embodiment, the present invention is directed to a process for preparing 2-methylnaphthalene in high selectivity wherein the process comprises reacting methanol and naphthalene in the vapor phase at a temperature in the range of about 500° to about 650° C. in the presence of an effective amount of activated alumina catalyst.

DETAILED DESCRIPTION

My process uses an amount of methanol to naphthalene, on a molar basis, in the range of about 0.5 to about 6.0. Preferably, on the same basis the amount of methanol to naphthalene is in the range of about 1 to about 4.

Suitable activated aluminas for use in my process are those characterized as having a low sodium content (e.g., less than 0.05 wt. % as $Na_2O$) and a high surface area (e.g., above 250 $m^2$/gm.). A particularly suitable alumina is available under the trademark CATAPAL®, which can be obtained from Conoco Chemicals Division of Continental Oil Company, Houston, Tex. CATAPAL® alumina has the following typical properties:

| Surface area | 260–400 $m^2$/gm |
|---|---|
| $Na_2O$, wt. % | less than 0.01 |
| Bulk Density | 7.5 to 25 lb/ft$^2$ |

The amount of catalyst is related to the liquid hourly space velocity $$LHSV = \frac{\text{volume of liquid per hour}}{\text{volume of catalyst}}$$

A suitable range of LHSV is about 0.1 to about 20. The preferred range is about 0.5 to about 2.5.

In some instances, it is desirable to use a solvent for the naphthalene, inasmuch as it has a melting point of 80° C. Solvents that are suitable are ones which do not serve as alkylating agents, which do not easily undergo alkylation, and which do not thermally degrade or undergo reaction at the required temperatures (425°–700° C.) for this process in the presence of alumina. Examples of suitable solvents include various hydrocarbon solvents such as benzene, toluene, hexane, ligroine and ethers such as ethyl ether.

My process prepares both 1-methylnaphthalene and 2-methylnaphthalene. Where there is no reason for preparing a product having a particularly high selectivity of 2-methylnaphthalene, the process can be operated at a temperature as low as about 425° C. A suprising feature of my process is that use of a higher temperature provides an increase in the selectivity of 2-methylnaphthalene in the product. When it is desired to prepare a product containing a high selectivity of 2-methylnaphthalene suitably the minimum temperature is about 550° C., preferably the minimum temperature is 570° C. In all instances the maximum temperature is 700° C., preferably 650° C.

The term "high selectivity" as used herein refers to at least 40 weight percent, preferably 50 weight percent, for the 2-methylnaphthalene.

The process can be operated at a pressure in the range of about 1 to about 70 atmospheres, preferably from about 10 to about 40 atmospheres.

As has been implied herein the process is operated on a continuous basis.

In order to illustrate the nature of the present invention still more clearly the following examples will be given. It is to be understood, however, that the invention is not to be limited to the specific conditions or details set forth in these examples except insofar as such limitations are specified in the appended claims.

EXAMPLE 1

A stainless steel tubular reactor (20"×⅝" I.D.) packed with crushed ⅛" CATAPAL® alumina was used. The feed consisted of naphthalene (64 g., 0.5 mole), methanol (32 g., 1.0 mole) and toluene (128 g.). The feed was preheated to 190° C. before entering the reactor, which was pressurized to 27.2 atmospheres with nitrogen at the start of the example. Runs were made at temperatures of 450° C., 524° C., and 599° C. and liquid hourly space velocities of 2.28, 0.94, and 0.94, respectively, in this example.

The product stream was collected in fractions of 5-30 g. The fractions were monitored by GLC (gas liquid chromatography). After run conditions had stabilized under a given set of conditions, several volumes of liquid feed were passed through the reactor under these conditions and then a sample was taken for analysis. The sample was analyzed by GLC and by spectroscopic data.

The results are shown in Table I.

EXAMPLE 2

The reactor was the same as shown in Example 1. The feed consisted of naphthalene (64 g., 0.5 mole), methanol (64 g., 2.0 mole) and toluene (128 g.). The feed was preheated to 360°-450° C. before entering the reactor, which was pressurized to 27.2 atmospheres at the start of the run. Runs were made at temperatures of 552° C. and 600° C. and liquid hourly space velocities of 0.67 and 0.68, respectively, in this example.

The product stream was collected in fractions of 22-44 g. The fractions were monitored by GLC (gas liquid chromatography). After run conditions had stabilized under a given set of conditions, several volumes of liquid feed were passed through the reactor under these conditions and then a sample was taken for analysis. The sample was analyzed by GLC and by spectroscopic data.

The results are shown in Table I.

1 to about 70 atmospheres in the presence of an effective amount of activated alumina.

2. The process of claim 1 wherein the amount of liquid feedstock to alumina catalyst is in the range of about 0.1 to about 20, expressed as volume of liquid in milliliters per hour per volume of catalyst in milliliters.

3. The process of claim 2 wherein the amount of methanol is about 1 to about 4 moles per mole of naphthalene.

4. The process of claim 3 wherein the amount of liquid feedstock to alumina catalyst is in the range of about 0.5 to about 2.5.

5. The process of claim 4 wherein the activated alumina has the following properties:

| Surface area | 260–400 m²/gm |
|---|---|
| Na₂O, wt. % | less than 0.01 |
| Bulk Density | 7.5 to 25 lb/ft² |

6. A process for preparing 2-methylnaphthalene in high selectivity wherein the process comprises reacting in vapor phase from about 0.5 mole to about 6.0 moles of methanol with 1 mole of naphthalene at a temperature in the range of about 550° to about 650° C. and a pressure in the range of about 1 to about 70 atmospheres in the presence of an effective amount of activated alumina.

7. The process of claim 6 wherein the amount of liquid feedstock to alumina catalyst is in the range of about 0.1 to about 20, expressed as volume of liquid in milliliters per hour per volume of catalyst in milliliters.

TABLE I

| Example | Run | Pressure (psig) | Temp (°C.) | LHSV | M[a] | Conv. | Sel.[b] (1) (w/o) | Sel.[b] (4) (w/o) | Sel.[b] (1 + 4) (w/0) |
|---|---|---|---|---|---|---|---|---|---|
| 1 | A | 400 | 450 | 2.28 | 2.0 | 6.0 | 32.7 | 59.2 | 91.9 |
| 1 | B | 400 | 524 | 0.94 | 2.0 | 14.2 | 34.0 | 46.6 | 80.6 |
| 1 | C | 400 | 599 | 0.94 | 2.0 | 17.8 | 49.7 | 24.6 | 74.3 |
| 2 | A | 400 | 552 | 0.67 | 4.0 | 25.4 | 42.4 | 33.6 | 76.0 |
| 2 | B | 400 | 600 | 0.68 | 4.0 | 20.4 | 59.2 | 15.4 | 74.6 |

[a]M = Moles methanol ÷ moles naphthalene in feed.
[b]Sel. (1) = 2-methylnaphthalene selectivity;
Sel. (4) = 1-methylnaphthalene selectivity;
Sel. (1 + 4) = combined selectivity for formation of 1- and 2-methylnaphthalenes.

Thus, having described the invention in detail, it will be understood by those skilled in the art that certain variations and modifications may be made without departing from the spirit and scope of the invention as defined herein and in the appended claims.

I claim:

1. A process for preparing a mixture of 1-methylnaphthalene and 2-methylnaphthalene wherein the process comprises reacting in vapor phase from about 0.5 mole to about 6.0 moles of methanol with 1 mole of naphthalene at a temperature in the range of about 425° C. to about 700° C. and a pressure in the range of about 8. The process of claim 7 wherein the amount of methanol is about 1 to about 4 moles per mole of naphthalene.

9. The process of claim 8 wherein the temperature is in the range of about 570° to about 650° C.

10. The process of claim 9 wherein the amount of liquid feedstock to alumina catalyst is in the range of about 0.5 to about 2.5.

11. The process of claim 10 wherein the term high selectivity refers to at least 40 weight percent based on 2-methylnaphthalene.

* * * * *